United States Patent [19]

Boden et al.

[11] 4,447,365

[45] * May 8, 1984

[54] 2-ETHYL HEXYL AND ISOBORNYL METHYL CARBONATES

[75] Inventors: Richard M. Boden, Monmouth Beach; Michael Licciardello, Farmingdale; Theodore J. Tyszkiewicz, Sayreville, all of N.J.

[73] Assignee: International Flavors & Fragrances Inc., New York, N.Y.

[ * ] Notice: The portion of the term of this patent subsequent to Jul. 26, 2000 has been disclaimed.

[21] Appl. No.: 458,964

[22] Filed: Jan. 18, 1983

Related U.S. Application Data

[62] Division of Ser. No. 322,872, Nov. 19, 1981, Pat. No. 4,390,463.

[51] Int. Cl.$^3$ .......................... C07C 69/96; A61K 7/46

[52] U.S. Cl. .................................................... 260/463

[58] Field of Search ......................................... 260/463

[56] References Cited

U.S. PATENT DOCUMENTS

| | | | |
|---|---|---|---|
| 4,033,993 | 7/1977 | Bruns et al. | 260/463 |
| 4,182,726 | 1/1980 | Illuminati et al. | 260/463 |
| 4,337,212 | 6/1982 | Sprecker et al. | 260/463 |
| 4,390,463 | 6/1983 | Boden et al. | 260/463 |
| 4,395,370 | 7/1983 | Boden et al. | 260/463 |

FOREIGN PATENT DOCUMENTS

| | | | |
|---|---|---|---|
| 1274837 | 5/1972 | European Pat. Off. | 260/463 |

OTHER PUBLICATIONS

Schving et al. Bull. Soc. Chim, vol. 43, pp. 857–859 (1928).

Amin et al. J. Chem. Soci., Perkins Trans. 2 (1979) (2) pp. 228–232.

*Primary Examiner*—Donald G. Daus
*Assistant Examiner*—Chabi C. Kalita
*Attorney, Agent, or Firm*—Arthur L. Liberman

[57] ABSTRACT

Described are the alkyl and bicycloalkyl methyl carbonates defined according to the structure:

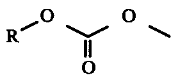

wherein R represents 2-ethyl hexyl, having the structure:

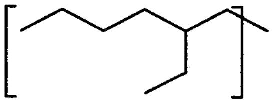

or isobornyl having the structure:

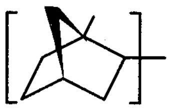

and uses thereof in augmenting or enhancing the aroma of perfume compositions, colognes and perfumed articles.

2 Claims, 12 Drawing Figures

GLC PROFILE FOR EXAMPLE I.

GLC PROFILE FOR EXAMPLE II.
BULKED FRACTIONS 3-5

NMR SPECTRUM FOR EXAMPLE I Fr. 6

IR SPECTRUM FOR FRACTION 6 FOR EXAMPLE I.

NMR SPECTRUM FOR EXAMPLE II.

I R SPECTRUM FOR EXAMPLE II.

GLC PROFILE FOR FRACTION 3 OF EXAMPLE III.

GLC PROFILE FOR FRACTION 6 OF EXAMPLE IV.

NMR SPECTRUM FOR FRACTION 3 OF EXAMPLE III

I R SPECTRUM FOR EXAMPLE III.

I R SPECTRUM FOR FRACTION 6 OF EXAMPLE IV.

2-ETHYL HEXYL AND ISOBORNYL METHYL CARBONATES

This application is a divisional of application for U.S. Letters Patent, Ser. No. 322,872 filed on Nov. 19, 1981, now U.S. Pat. No. 4,390,463 issued on June 28, 1983.

BACKGROUND OF THE INVENTION

The instant invention provides novel alkyl, aralkyl, alkadienyl and bicycloalkyl methyl carbonates defined according to the structure:

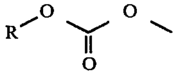

wherein R represents 2-ethyl hexyl, linalyl, isobornyl and 1-phenylethyl and uses thereof in augmenting or enhancing the aroma of consumable materials.

Materials which can provide spicy, caryophyllene-like, bergamot-like, piney, rosey, green, woody and balsamic aroma nuances are well known in the art of perfumery. Man of the natural substances which provide such fragrances and contributes the desired nuances to perfumery compositions are high in cost, vary in quality from one batch to another and/or are generally subject to the usual variations of natural products.

The prior art contains a large number of teachings regarding the use of organic carbonates in augmenting or enhancing the aroma of perfumes. Thus, U.S. Pat. No. 4,033,993 discloses the use of organic carbonates defined according to the structure:

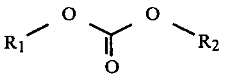

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynl having from 2 to 5 carbon atoms.

U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having an herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

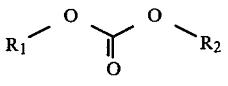

according to the reaction:

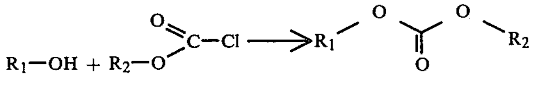

where $R_1$ and $R_2$ are defined as above.

In addition, U.S. Pat. No. 4,080,309 describes the perfume use of the carbonates defined according to the structure:

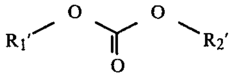

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of U.S. Pat. No. 4,080,309 are indicated to be prepared according to the reaction:

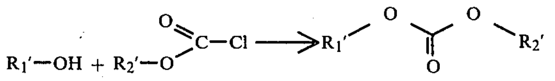

Arctander "Perfume And Flavor Chemicals (Aroma Chemicals) Volume I", discloses the use of certain ethyl carbonates in perfumery. Thus, Arctander at monograph 1661 discloses hexyl ethyl carbonate thusly:

> "This ester is rarely offered under its proper chemical name, but it enters several perfume specialties as part of the ethereal-refreshing topnote used in a great variety of perfumes-floral, herbacious, citrusy, etc. It seems to have a good ability for "mellowing" a fragrance and introducing a "natural" note . . . "

At monograph 1445 Arctander discloses geranyl ethyl carbonate to have a sweet and mellow and rosy and warm tenacious odor . . . sweeter than geraniol but not fruity like geranyl acetate, rather a mellow and an almost musky way.

At monograph 2528 of Volume II, Arctander states that phenyl ethyl carbonate having the structure:

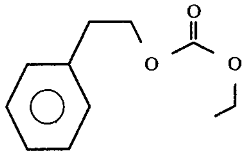

has a mellowing effect upon the aliphatic aldehydes and aldehydic top notes and basis. It is stated that it is interesting by its effect of "lifting" a musk odor so that the musk becomes preceptible at a much earlier stage of the perfume evaporation.

Nothing in the prior art, however, discloses the alkyl, aralkyl, alkadienyl and bicycloalkyl methyl carbonates of our invention having the specific fragrance nuances of the compounds of our invention.

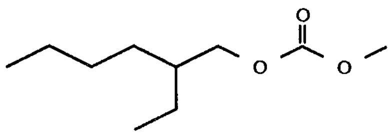

Figure 2:
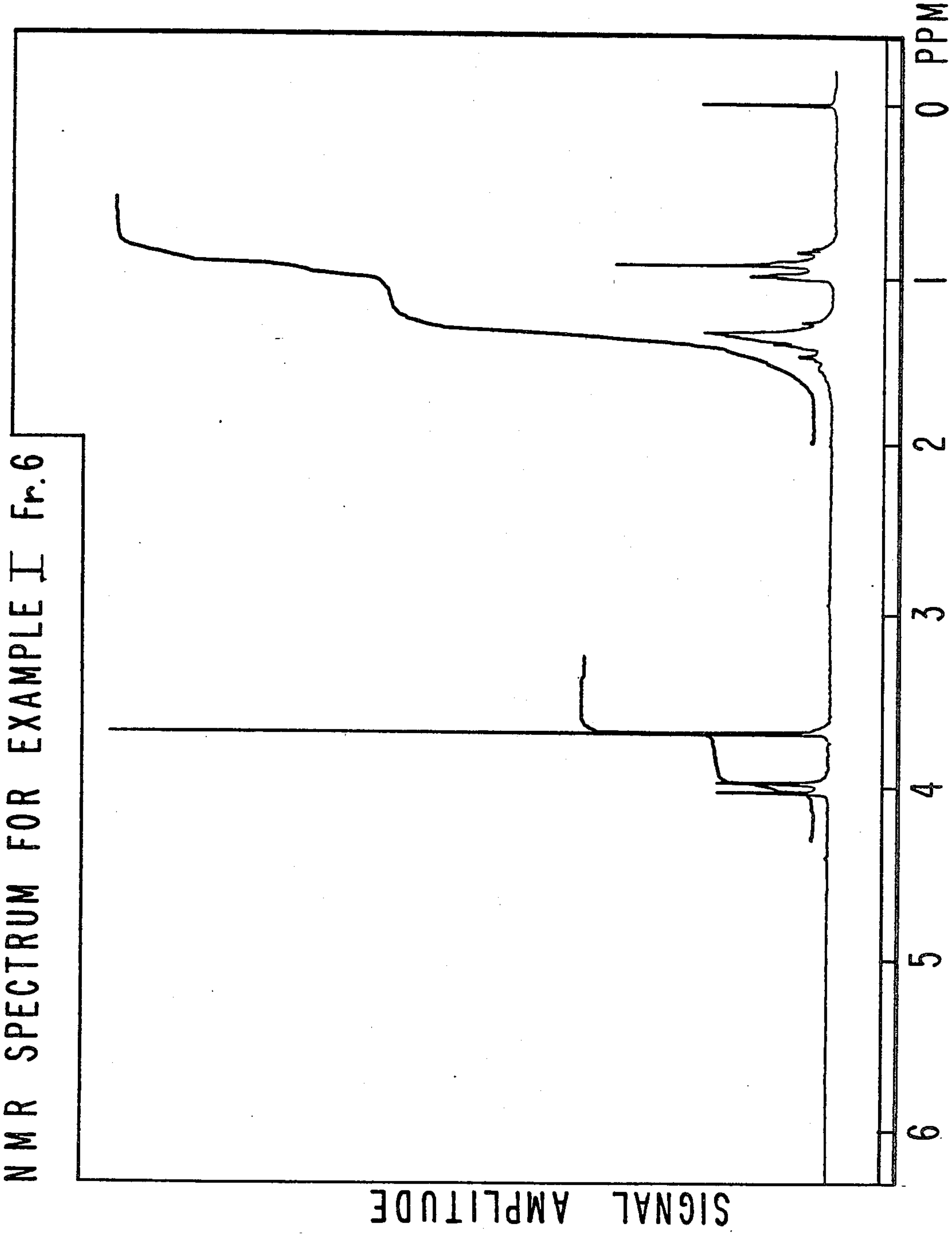

FIG. 2 is the NMR spectrum for fraction 6 of the distillation product of the reaction product of Example I containing the compound having the structure:

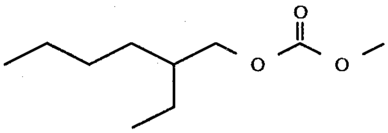

Figure 3:
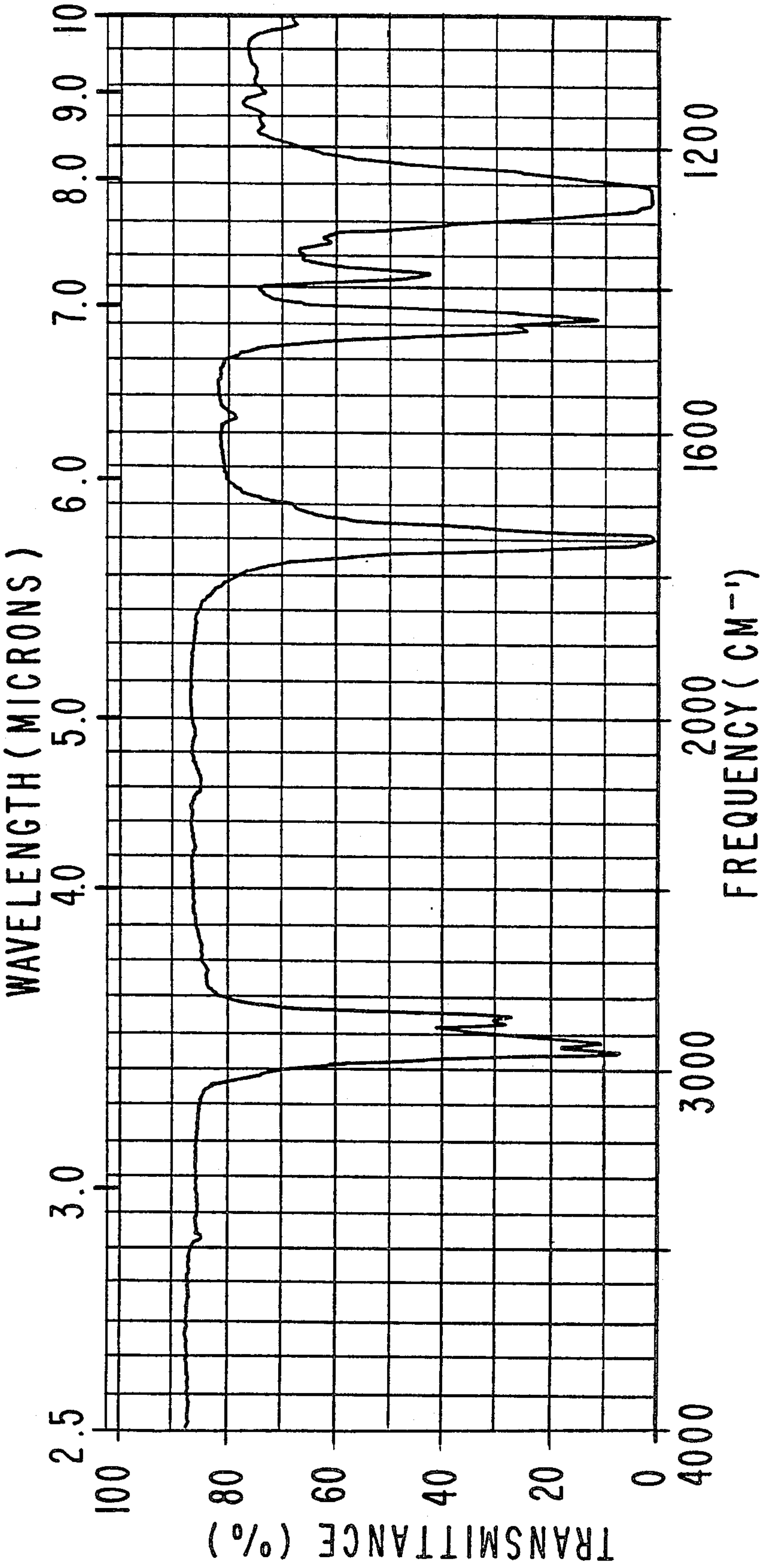

FIG. 3 is the infra-red spectrum for fraction 6 of the distillation product of the reaction product of Example I containing the compound having the structure:

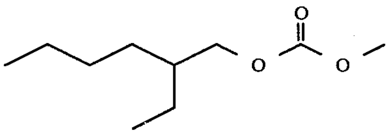

Figure 4:
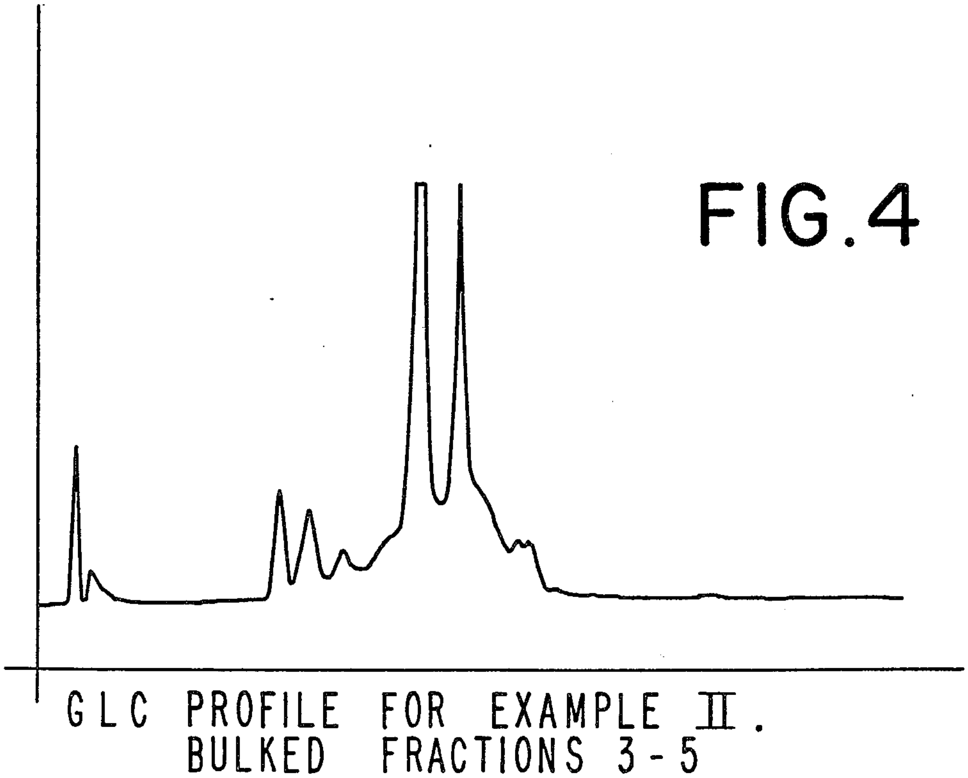

FIG. 4 is the GLC profile for bulked fractions 3-5 of the distillation product of the reaction product of Example II containing the compounds having the structures:

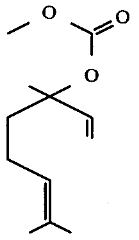
and
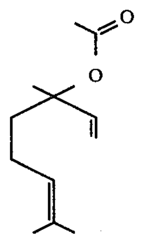

Figure 5:
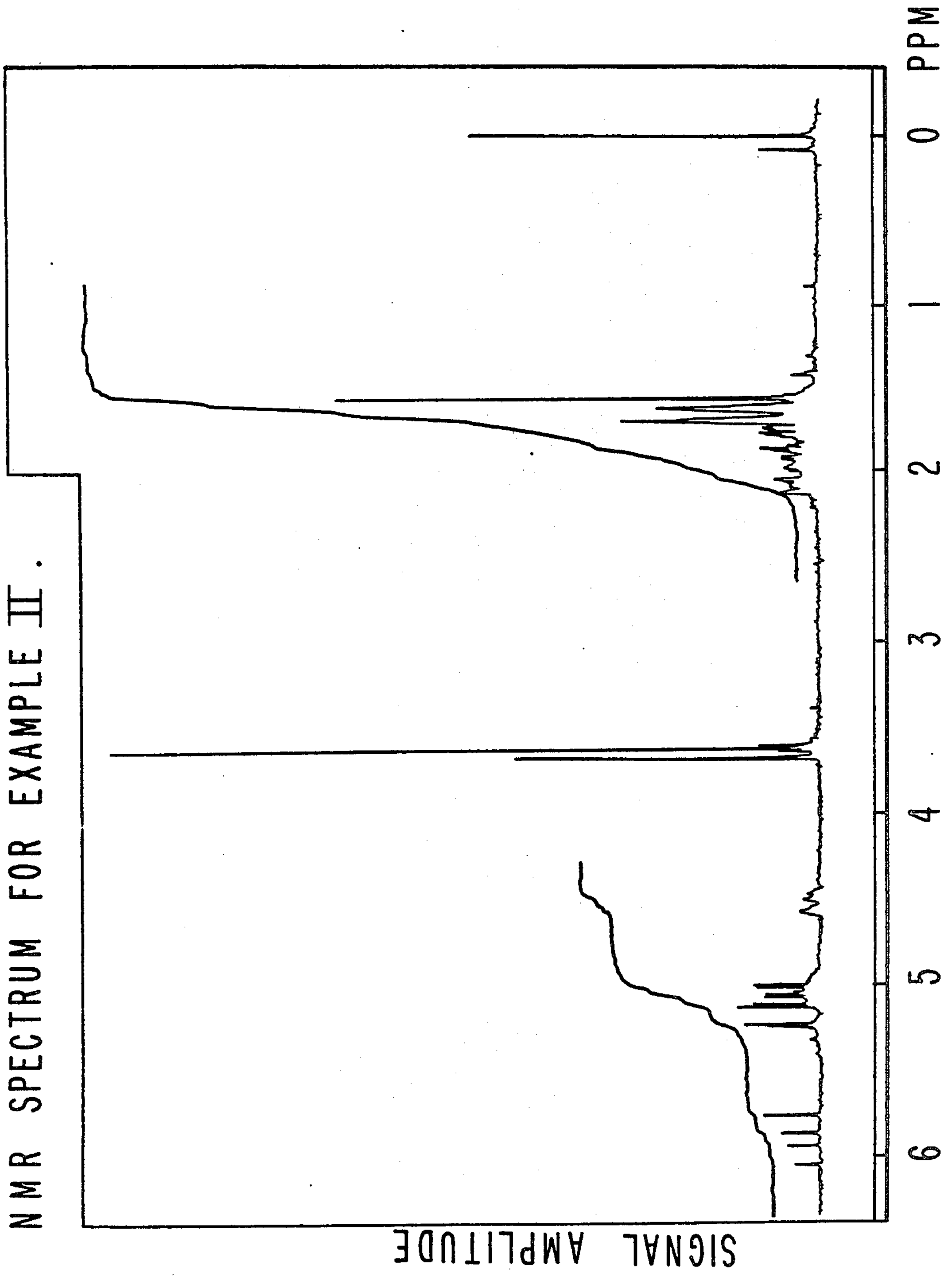

FIG. 5 is the NMR spectrum for bulked fractions 3-5 of the distillation product of the reaction product of Example II containing the compounds having the structures:

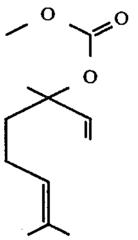
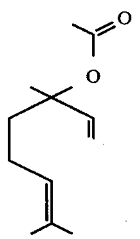

Figure 6:
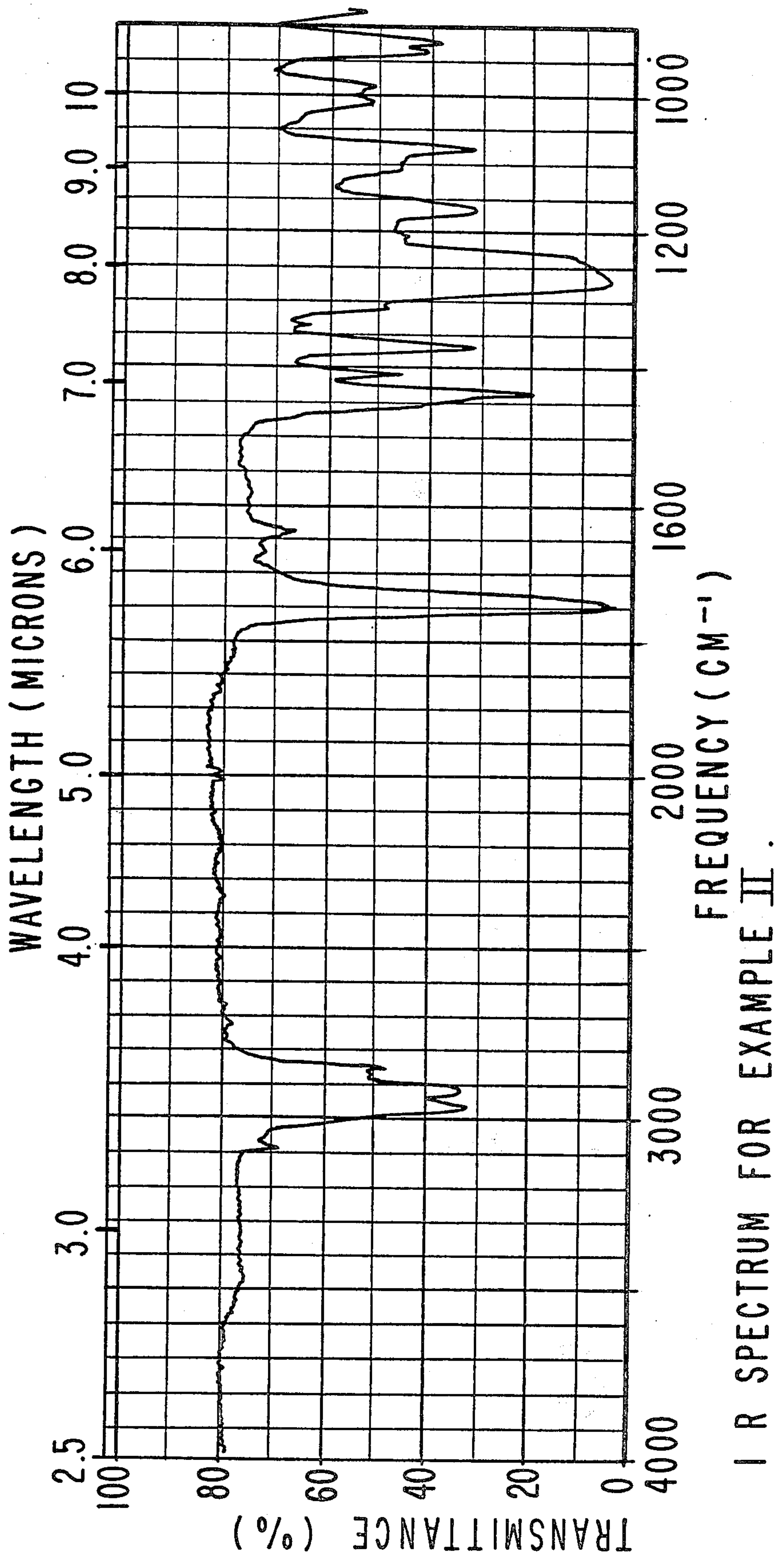

FIG. 6 is the infra-red spectrum for bulked fractions 3-5 of the distillation product of the reaction product of Example II containing the compounds having the structures:

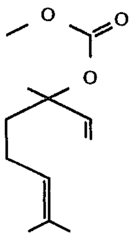
and
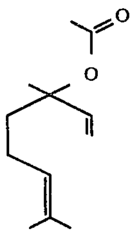

Figure 7:
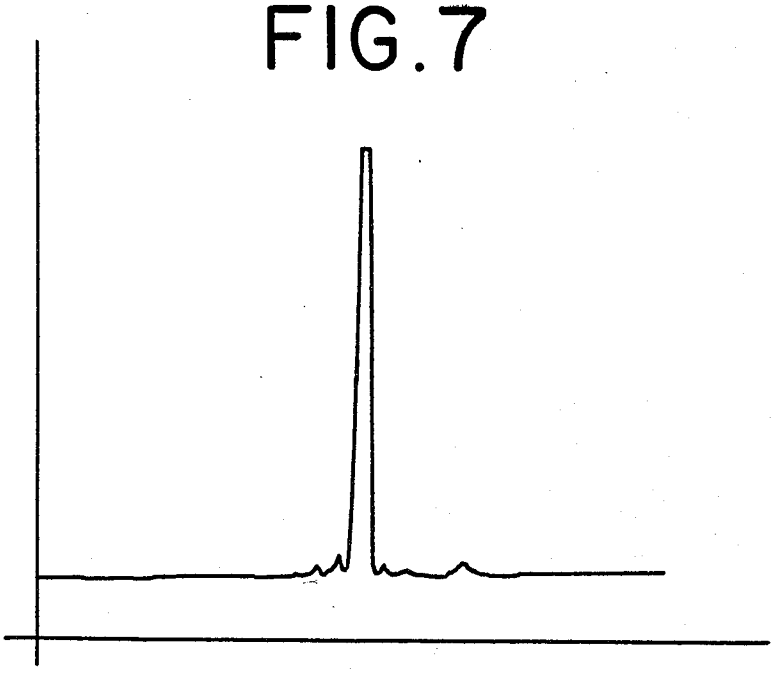

FIG. 7 is the GLC profile for fraction 3 of the distillation product of the reaction product of Example III containing the compound having the structure:

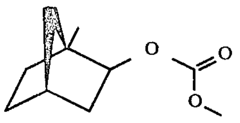

Figure 8:
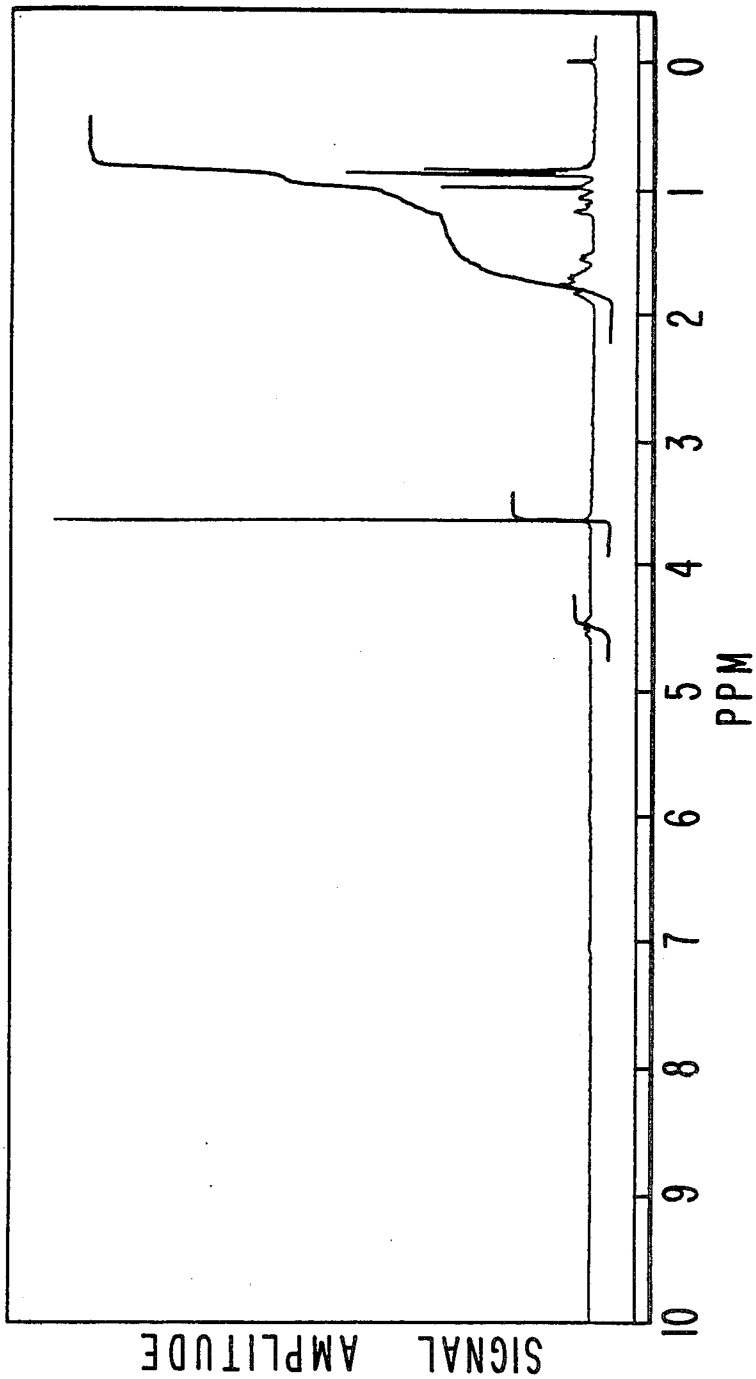

FIG. 8 is the NMR spectrum for fraction 3 of the distillation product of the reaction product of Example III containing the compound having the structure:

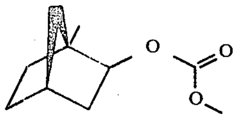

Figure 9:
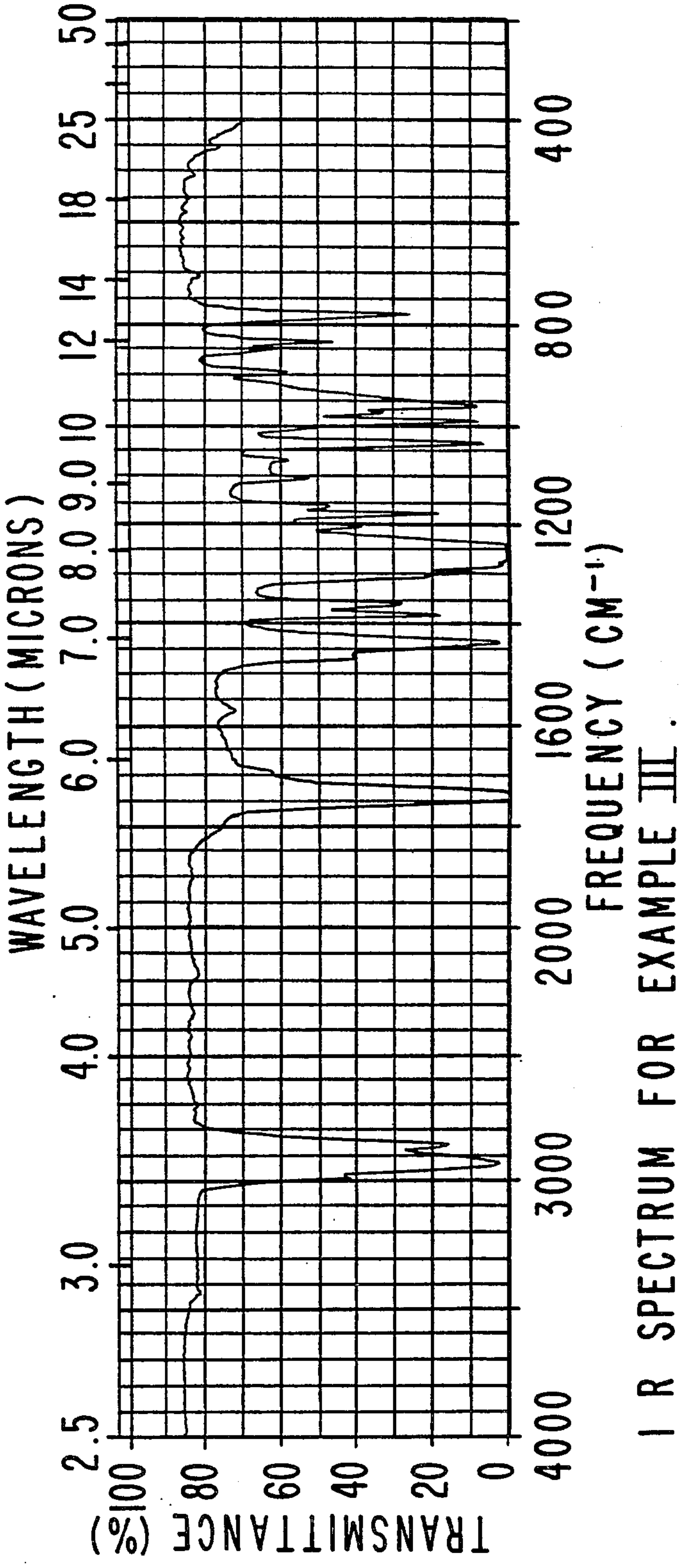

FIG. 9 is the infra-red spectrum for fraction 3 of the distillation product of the reaction product of Example III containing the compound having the structure:

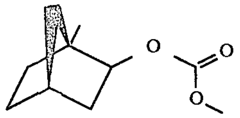

Figure 10:
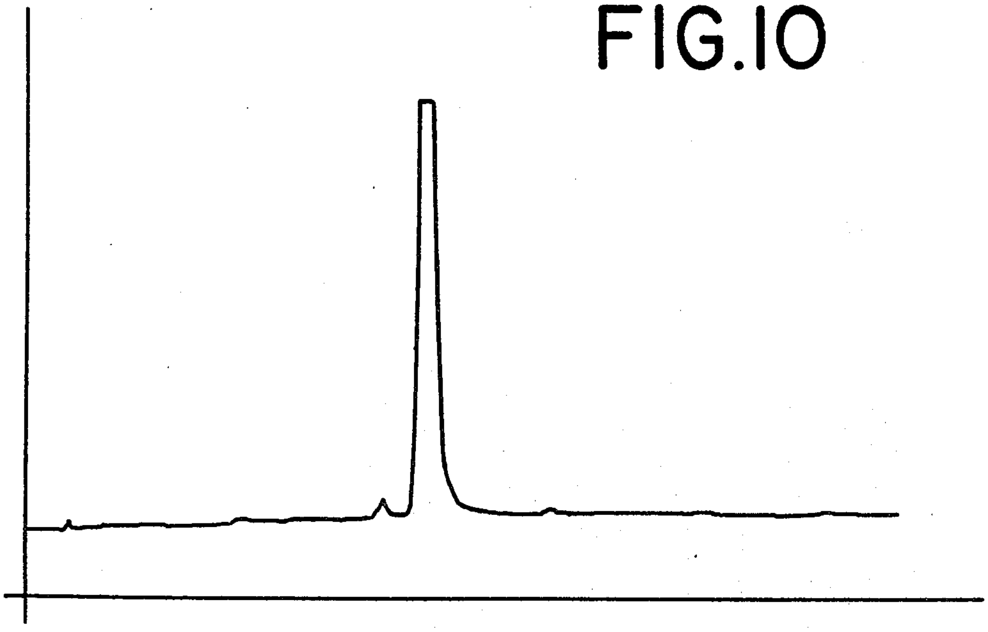

FIG. 10 is the GLC profile for fraction 6 of the distillation product of the reaction product of Example IV containing the compound having the structure:

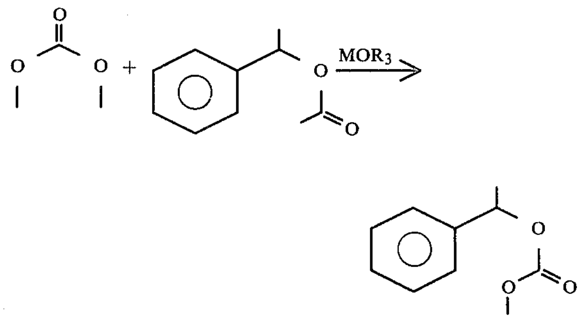

Figure 11:
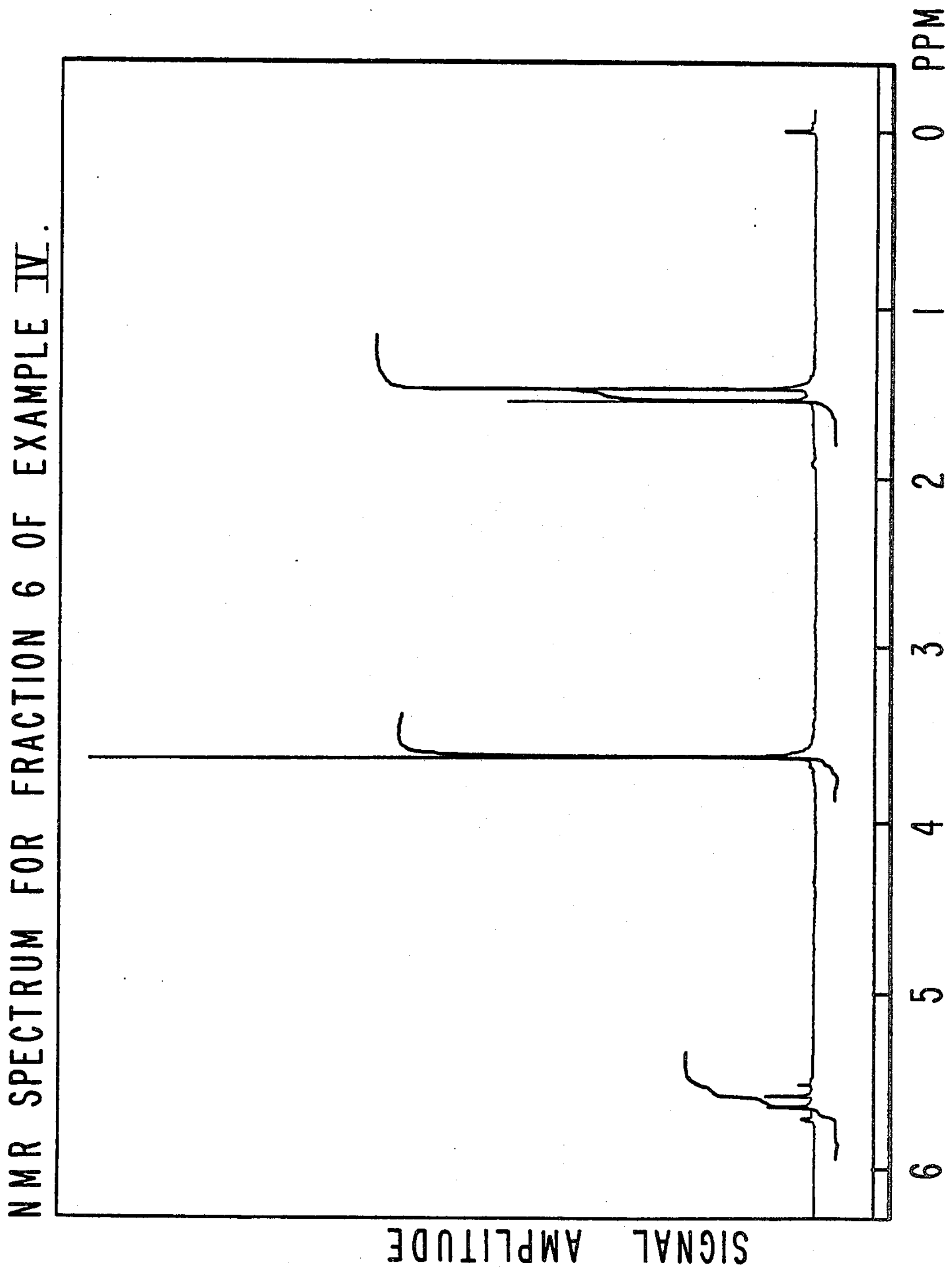

FIG. 11 is the NMR spectrum for fraction 6 of the distillation product of the reaction product of Example IV containing the compound having the structure:

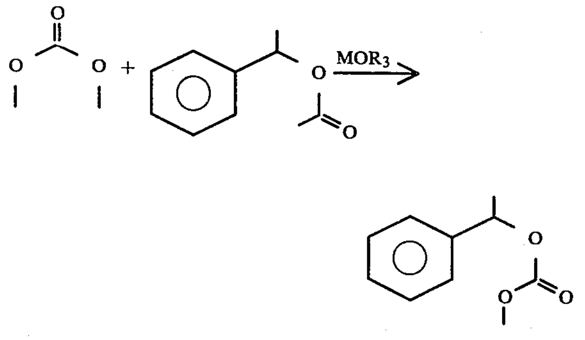

Figure 12:
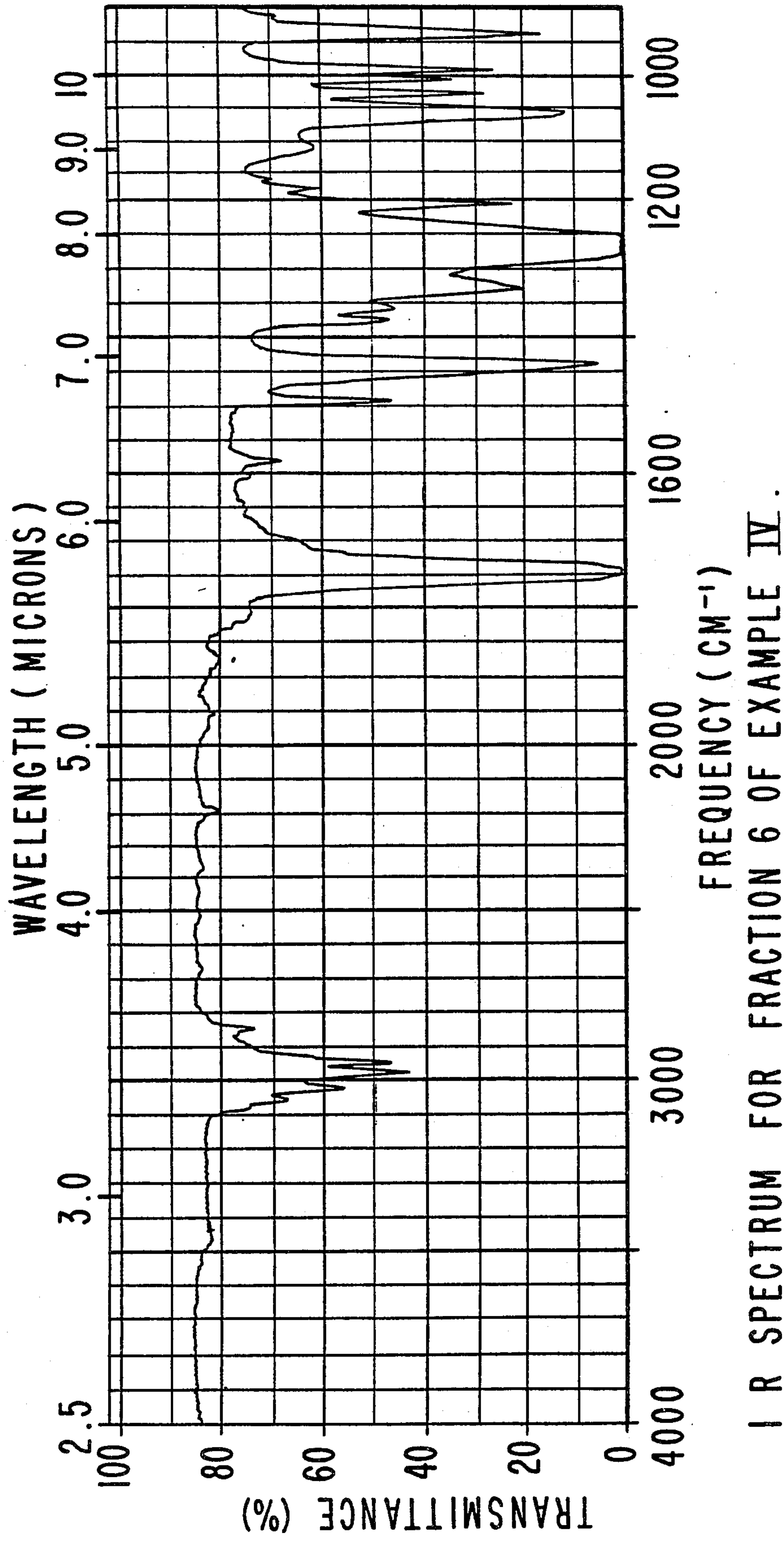

FIG. 12 is the infra-red spectrum for fraction 6 of the distillation product of the reaction product of Example IV containing the compound having the structure:

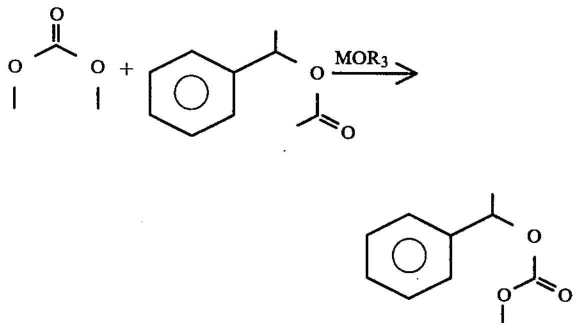

THE INVENTION

The present invention provides the compounds defined according to the structure:

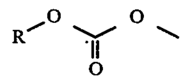

wherein R is 2-ethyl hexyl having the structure:

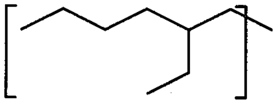

linalyl having the structure:

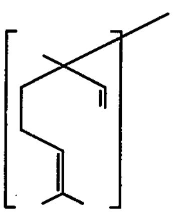

isobornyl having the structure:

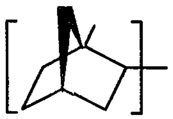

or 1-phenyl ethyl having the structure:

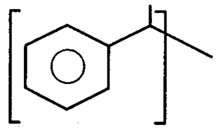

The present invention also provides an economical efficient process for synthesizing the compounds having the structure:

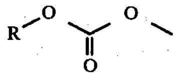

by reacting dimethyl carbonate with an alkyl, aralkyl, alkadienyl or bicycloalkyl acetate in the presence of an alkali metal alkoxide according to the reaction:

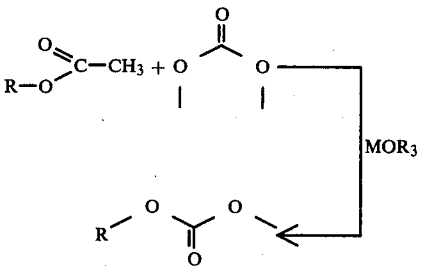

wherein R represents 2-ethyl hexyl, linalyl, isobornyl or 1-phenylethyl; wherein M represents alkali metal such as sodium, potassium and lithium and wherein $R_3$ represents lower alkyl such as methyl, ethyl, propyl, n-butyl and tertiary butyl.

The present invention also provides processes for using the compounds defined according to the generic structure:

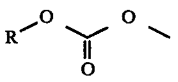

for their organoleptic properties in augmenting or enhancing the organoleptic properties of consumable materials, that is, the aroma of perfumes, colognes and perfumed articles (such as perfumed polymers, solid or liquid cationic, anionic, nonionic or zwitterionic detergents, soaps, fabric softener compositions, drier-added fabric softener articles such as BOUNCE® registered trademark of the Procter & Gamble Company of Cincinnati, Ohio, fabric brighteners, cosmetic powders, bath preparations, hair preparations such as hair sprays and shampoos).

In addition, the alkyl, aralkyl, alkadienyl and bicycloalkyl methyl carbonates of our invention may be prepared by first reacting an alkyl, aralkyl, alkadienyl or bicycloalkyl formate with dimethyl carbonate according to the reaction:

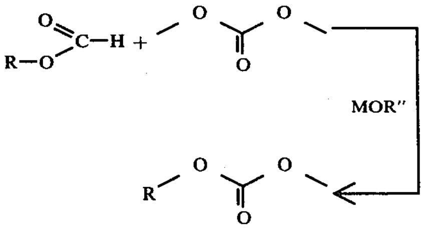

in the presence of an alkali metal alkoxide such as sodium methoxide, sodium ethoxide, sodium-t-butoxide, potassium methoxide, potassium ethoxide and potassium-t-butoxide. The reaction between the formate ester and the dimethyl carbonate takes place in the absence of any additional solvent. The mole ratio range of dimethyl carbonate:formate ester may vary from 3 moles dimethyl carbonate:0.5 moles formate ester down to 1 mole dimethyl carbonate:1 mole formate ester. It is preferred that the mole ratio of dimethyl carbonate: formate ester be about 2:1. The molar concentration in the reaction mass of the alkali metal alkoxide catalyst may vary from about 0.005 up to about 0.01 with a molar concentration of about 0.05 moles per liter being preferred.

The reaction temperature range in each of the above cases may vary from about 50° C. up to about 100° C. and the reaction pressure may vary from atmospheric pressure up to about 10 atmospheres. Higher temperature of reaction necessitates higher pressure over the reaction mass in order to prevent the reaction product from evaporating therefrom.

At the end of the reaction, the reaction product is purified according to standard procedures such as fractional distillation and, if necessary, chromatographic separation as by high pressure liquid chromatography or GLC (vapor phase chromatography).

Examples of reaction products prepared in accordance with the process of our invention and their organoleptic properties are as follows:

TABLE I

| Reaction Product | Aroma Properties |
|---|---|
| 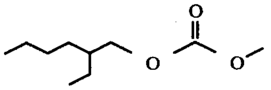 | A spicy, caryophyllene-like, corduroy-like aroma. |
| Mixture of compounds having the structures: 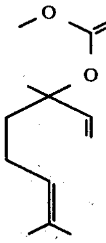 and 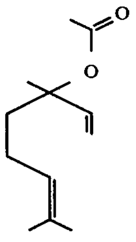 produced according to Example II, infra. | A bergamot aroma. |
| Compound having the structure: | An intense, piney aroma. |

TABLE I-continued

| Reaction Product | Aroma Properties |
|---|---|
| 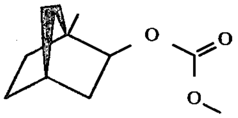 prepared according to Example III, infra. | |
| Compound having the structure: 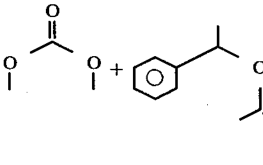 | A floral, rosey, green, woody-balsamic, spicy, cinnamon-like aroma profile. |

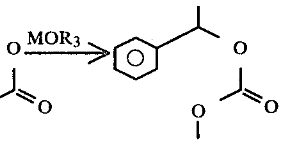

The alkyl, aralkyl, alkadienyl and bicycloalkyl methyl carbonates of our invention can be used to contribute spicy, caryophyllene-like, bergamot-like, piney, rosey, green, woody and balsamic aroma nuances to perfumed compositions and perfumed articles such as solid or liquid cationic, anionic, nonionic or zwitterionic detergents, perfumed polymers, fabric softener compositions, fabric softener articles, optical brighteners, fabric conditioners, hair preparations, shampoos and hair sprays. As olfactory agents, the alkyl, aralkyl, alkadienyl and bicycloalkyl methyl carbonates of our invention can be formulated into or used as components of a "perfume composition".

The term "perfume composition" is used herein to mean a mixture of organic compounds including, for example, alcohols, aldehydes, ketones, nitriles, ethers, lactones, esters other than the carbonates of our invention, and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topy notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of alkyl, aralkyl, alkadienyl and/or bicycloalkyl methyl carbonates of our invention which will be effective in perfume compositions depends upon many factors including the other ingredients, their amounts and the effects which are desired. It has been found that perfume compositions containing as little as 0.1% of the alkyl, aralkyl, alkadienyl and/or bicycloalkyl methyl carbonates of our invention or even less and perfume compositions containing as much as 70% by weight of the alkyl, aralkyl, alkadienyl and bicycloalkyl methyl carbonates of our invention can be used to impart interesting spicy, caryophyllene-like, bergamot-like, piney, rosey, green, woody and balsamic aroma nuances to perfumed articles, perfumed compositons and colognes. Such perfumed articles include fabric softener compositions, drier-added fabric softener articles, cosmetic powders, talc, solid or liquid anionic, cationic, nonionic or zwitterionic detergents and perfumed polymers. The amount employed can range up to 70% and will depend upon considerations of cost, nature of the end product and the effect desired on the finished product and particular fragrance sought.

Thus, the alkyl, aralkyl, alkadienyl and bicycloalkyl methyl carbonates of our invention can be used alone or in a perfume composition as an olfactory component, in solid or liquid anionic, cationic, nonionic or zwitterionic detergents (including soaps), perfumed polymers (those which are microporous and those which are macroporous and contain particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler a solid or liquid cationic, anionic, nonionic or zwitterionic detergent or of a cosmetic powder, as little as 0.01% of one or more of the alkyl, aralkyl, alkadienyl and/or bicycloalkyl methyl carbonates of our invention will suffice to provide an interesting spicy, caryophyllene-like, bergamot-like, piney, rosey, green, woody and/or balsamic aroma. Generally, no more than 0.8% of the alkyl, aralkyl, alkadienyl and/or bicycloalkyl methyl carbonates of our invention are required.

In addition, the perfume compositions of our invention can contain a vehicle or carrier for the alkyl, aralkyl, alkadienyl and/or bicycloalkyl methyl carbonates of our invention alone or with other ingredients. The vehicle can be a liquid such as an alcohol such as ethanol, a glycol such as propylene glycol or the like. The carrier can be an absorbent soild such as gum (e.g., xanthan gum, guar gum or gum arabic) or components for encapsulating the composition as by coacervation (using gelatin) or by polymerization using for example (a) urea formaldehyde polymer.

The following Examples I, II, III and IV set forth processes for preparing the alkyl, aralkyl, alkadienyl and bicycloalkyl methyl carbonates of our invention. The examples following Example IV, e.g., Examples V, et. seq. represent methods for using the alkyl, aralkyl, alkadienyl and bicycloalkyl methyl carbonates of our invention for their organoleptic properties.

Unless otherwise indicated, all parts and percentages are by weight.

EXAMPLE I

Preparation of 2-Ethyl hexyl methyl carbonate

Reaction:

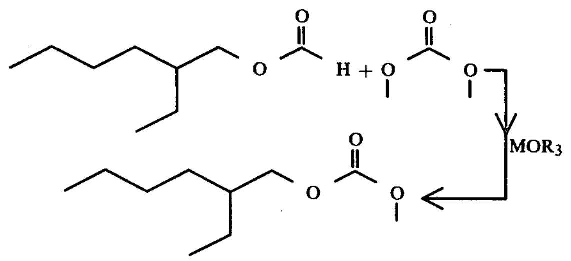

where M is sodium and $R_3$ is methyl.

Into a 2 liter reaction flask equipped with Bidwell take-off apparatus, nitrogen blanket thermometer and reflux condenser is placed 355.4 grams (332.5 ml) of dimethyl carbonate and 16 grams of sodium methoxide.

20 ml of 2-ethyl-1-hexyl formate is then added to the reaction mass and the reaction mass is heated to 80° C.

While maintaining the reaction temperature at 70°-82° C., and while removing formic acid from the reaction mass, 362 grams of 86% 2-ethyl-1-hexyl formate is added from the addition funnel. The addition time is 1 hour.

At the end of the reaction, the reaction mass is stirred for an additional 1 hour at 79° C.

The aqueous layer is removed and the organic layer is washed with 2-1 liter portions of water to a pH of between 6 and 7. The organic layer is then distilled on a 6" stone pegged column yielding the following fractions:

| Fraction Number | Vapor Temp. (°C.) | Liquid Temp. (°C.) | Pressure Vacuum mm/Hg | Weight of Fraction |
|---|---|---|---|---|
| 1 | 72/68 | 94/93 | 5/28 | 49.0 |
| 2 | 67 | 90 | 3.2 | 51.0 |
| 3 | 60 | 88 | 3.0 | 46.0 |
| 4 | 62 | 90 | 3.0 | 51.0 |
| 5 | 60 | 99 | 2.8 | 46.0 |
| 6 | 58 | 123 | 2.8 | 32.0 |
| 7 | 139 | 174 | 2.8 | 49.0 |
| 8 | 132 | 219 | 2.8 | 35.0 |

Figure 1:
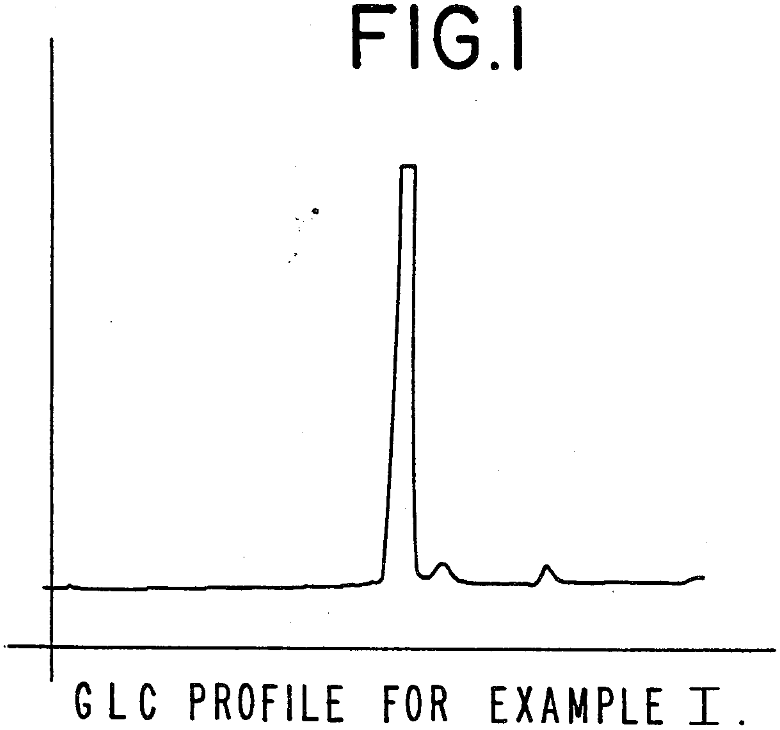
FIG. 1 is the GLC profile for fraction 6 of the distillation product of the reaction product of Example I containing the compound having the structure.

FIG. 1 is the GLC profile for fraction 6 of the foregoing distillation product (conditions: 12% SF-96 column, 6'×¼", programmed at 100°-220° C. at 8° C. per minute.

FIG. 2 is the NMR spectrum for fraction 6 of the foregoing distillation.

FIG. 3 is the infra-red spectrum for fraction 6 of the foregoing distillation.

EXAMPLE II

Preparation of mixture of linalyl methyl carbonate and linalyl acetate

Reaction:

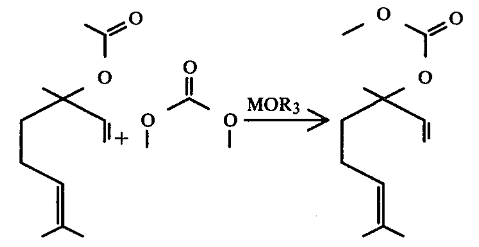

wherein M is sodium and $R_3$ is methyl.

Into a 1 liter reaction flask equipped with thermometer condenser, Bidwell trap and nitrogen blanket apparatus is placed 11.9 grams (0.22 moles) of sodium methoxide and 261 grams (247 ml) (2.93 moles) of dimethyl carbonate. 20 ml linalyl acetate is added to the mixture. The reaction mass is heated to reflux (82° C.) and while refluxing at 82°-89° C. over a period of 1 hour, 270 grams of linalyl acetate is added (total linalyl acetate: 1.46 moles). The reaction mass is heated at 89°-97° C. for a period of 4 hours at which point in time it is then cooled to room temperature and transferred to a separatory funnel. The reaction mass is then washed with:

1 liter portion of water

1—1 liter portion of saturated sodium chloride

1—1 liter portion of saturated sodium chloride

The reaction mass is then distilled on a 6" stone packed column yielding the following fractions:

| Fraction Number | Vapor Temp. (°C.) | Liquid Temp. (°C.) | Pressure Vacuum mm/Hg. | Weight of Fraction |
|---|---|---|---|---|
| 1 | 49/65 | 84/90 | 30/35 | 46.0 |
| 2 | 69 | 99 | 3.0 | 52.0 |
| 3 | 72 | 100 | 3.0 | 40.0 |
| 4 | 73 | 103 | 2.8 | 48.0 |
| 5 | 76 | 114 | 2.8 | 50.0 |
| 6 | 72 | 156 | 2.8 | 19.0 |

Bulked fractions 3-5 have an interesting strong bergamot aroma. NMR, IR mass spectrum analysis yield the information that the resulting product is a mixture of compounds defined according to the structures:

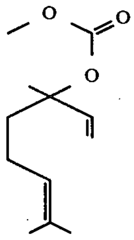

and

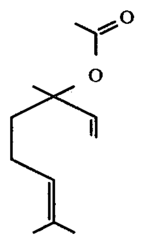

FIG. 4 is the GLC profile for bulked fractions 3-5 (conditions: 12% SF-96 column, 6'×¼"; programmed at 100°-220° C. at 8° C. per minute).

FIG. 5 is the NMR spectrum for bulked fractions 3-5 of the foregoing distillation.

FIG. 6 is the infra-red spectrum for bulked fractions 3-5 of the foregoing distillation.

EXAMPLE III

Preparation of methyl isobornyl carbonate

Reaction:

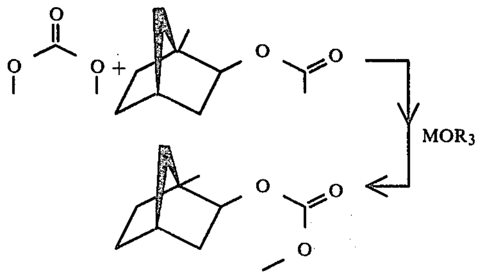

wherein M is sodium and $R_3$ is methyl.

Into a 3 liter reaction flask equipped with heating mantle stirrer reflux condenser, Bidwell trap, thermometer and addition funnel is placed 1250 grams (14 moles) of dimethyl carbonate and 10 grams of sodium methoxide. The resulting mixture is heated to 80° C. and while maintaining the reaction mixture at 80° C., over a period of 2 hours, 908 grams (5.3 moles) of isobornyl acetate is added thereto. The reaction mixture is maintained at 70°-89° C. over a period of 2 more hours. At the end of the reaction, the reaction mixture is washed with one volumn of 5% acetic acid and 1 liter of saturated sodium chloride.

The resulting mixture is then distilled on a 2" splash column yielding the following fractions:

| Fraction Number | Vapor Temp. (°C.) | Liquid Temp. (°C.) | Pressure Vacuum mm/Hg | Weight of Fraction |
|---|---|---|---|---|
| 1 | 51/95 | 93/102 | 7/5 | |
| 2 | 94 | 104 | 5.0 | |
| 3 | 95 | 104 | 5.0 | |
| 4 | 98 | 110 | 5.0 | |
| 5 | 101 | 140 | 5.0 | |
| 6 | | | | |
| 1 | /98 | /107 | /6 | |

FIG. 7 is the GLC profile for fraction 3 which contains the compound defined according to the structure:

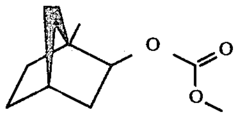

FIG. 8 is the NMR spectrum for fraction 3 of the foregoing distillation product.

FIG. 9 is the infra-red spectrum for fraction 3 of the foregoing distillation product.

EXAMPLE IV

Preparation of styrallyl methyl carbonate (methyl-1-phenyl ethyl carbonate)

Reaction:

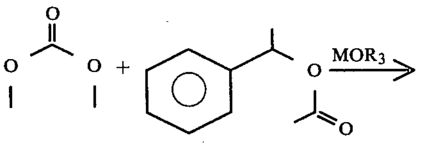

-continued

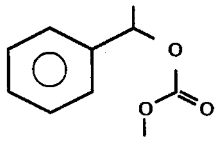

wherein M is sodium and $R_3$ is methyl.

Into a 2 liter reaction flask equipped with stirrer thermometer, reflux condenser, addition funnel, nitrogen atmosphere apparatus and Bidwell trap is placed 720 grams (8 moles) of dimethyl carbonate and 32.4 grams (0.6 moles) of sodium methoxide. 20 ml of styrallyl acetate is then added to the reaction mass and the reaction mass is heated to 80° C. Dropwise over a period of 1 hour, 640 grams of styrallyl acetate is added to the reaction mass while maintaining the reaction mass at 81° C. with stirring. The reaction mass is then stirred at 81°-90° C. for a period of 6 hours.

The reaction mass is then quenched with an equivalent volume of acetic acid.

The lower organic layer is removed and the upper aqueous phase is separated therefrom. The organic layer is washed with two 1.5 liter portions of water to pH of 7.

The reaction product is then distilled on a 4" stone packed column yielding the following fractions:

| Fraction Number | Vapor Temp. (°C.) | Liquid Temp. (°C.) | Pressure Vacuum mm/Hg | Weight of Fraction |
|---|---|---|---|---|
| 1 | 26/33 | 43/98 | 14/8 | 15.0 |
| 2 | 113 | 103 | 8.0 | |
| 3 | 90 | 108 | 3.0 | |
| 4 | 82 | 103 | 3.0 | |
| 5 | 79 | 105 | 3.0 | |
| 6 | 80 | 128 | 3.0 | |
| 7 | 145 | 210 | 3.0 | |

The resulting product has a floral, rosey, green, woody, balsamic, spicy, cinnamic-like aroma.

The GLC, NMR, IR mass spectral analysis yield the information that the compound prepared above has the structure:

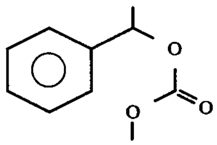

FIG. 10 is the GLC profile for fraction 6 of the foregoing distillation (conditions: 12% SF-96, 6'×¼" column programmed at 100°-220° C. at 8° C. per minute).

FIG. 11 is the NMR spectrum for fraction 6 of the foregoing distillation.

FIG. 12 is the infra-red spectrum for fraction 6 of the foregoing distillation.

EXAMPLE V

Preparation of honey fragrance

The following mixture is prepared:

| Ingredients | Parts by Weight |
|---|---|
| Phenylacetic acid | 70.0 |
| Coumarin | 20.0 |
| Phenylethyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| Methyl-2-ethyl-1-hexyl carbonate prepared according to Example I | 30.0 |

The methyl-2-ethyl-1-hexyl carbonate prepared according to Example I imparts a spicy, caryophyllene-like, corduory aroma nuance to this honey fragrance formulation.

EXAMPLE VI

Jasmine perfume formulations

The following mixture is prepared:

| Ingredients | Parts by Weight |
|---|---|
| Mixture of Linalyl acetate and methyl linalyl carbonate prepared according to Example II, bulked, fractions 3-5 | 230 |
| Benzyl acetate | 150 |
| Linalool | 60 |
| Hydroxy citronellal | 60 |
| Ylang Oil | 40 |
| Methyl jasmonate | 25 |
| Benzyl salicylate | 15 |
| Geranyl acetate | 25 |
| n-undecanal | 25 |
| Para-cresyl phenyl acetate | 10 |
| Phenylethyl acetate | 20 |
| Phenylethyl alcohol | 50 |
| Indol | 20 |
| Coumarin | 12 |

The mixture of linalyl acetate and methyl linalyl carbonate produced according to Example II adds an excellent bergamot undertone as to this jasmine formulation.

EXAMPLE VII

Pine needle oil formulation

The following mixture is prepared:

| Ingredients | Parts by Weight |
|---|---|
| Turpentine gum oil | 100 |
| Limonene | 70 |
| Gum camphor | 10 |
| Isobornyl acetate | 50 |
| Borneol | 30 |
| Methyl isobornyl carbonate | 110 |

The methyl isobornyl carbonate produced according to Example III, fraction 3, adds a natural piney/woody/smokey aroma to this pine needle oil fragrance.

EXAMPLE VIII

Herbal fragrance formulation

The following mixture is prepared:

| Ingredients | Parts by Weight |
|---|---|
| Amyl cinnamic aldehyde | 20 |
| Phenyl acetaldehyde dimethyl acetal | 4 |
| Thyme oil white | 8 |
| Sauge sclaree French | 8 |
| Galbanum oil | 4 |
| Juniper berry oil | 10 |
| Methyl octinyl carbonate | 4 |
| Linonyl acetate | 2 |
| Dihydro methyl jasmonate | 10 |
| Styrallyl methyl carbonate prepared according to Example IV | 10 |

The styrallyl methyl carbonate prepared according to Example IV gives to this herbal fragrance formulation an excellent floral, rosey, green, woody, balsamic, spicy, cinnamin-like undertone causing it to be much more esthetically pleasing and more "rain forest"-like.

EXAMPLE IX

Preparation of cosmetic powder compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| Methyl-2-ethyl-1-hexyl carbonate prepared according to Example I, fraction 6 | A spicy, caryophyllene-like corduory aroma profile. |
| Mixture of linalyl acetate and methyl linalyl carbonate prepared according to Example II (bulked fractions 3-5). | A bergamot aroma. |
| Methyl isobornyl carbonate prepared according to Example III (fraction 3). | An intense piney aroma. |
| Methyl 1-phenyl ethyl carbonate prepared according to Example IV (fraction 6). | A floral, rosey, green, woody, balsamic, spicy, cinnamin-like aroma. |
| Perfume composition prepared according to Example V. | A honey fragrance with spicy, caryophyllene-like corduory undertones. |
| Fragrance prepared according to Example VI. | A jasmine aroma with bergamot-like undertones. |
| Fragrance prepared according to Example VII. | A pine needle aroma with natural piney, smokey, rain forest-like aroma nuances. |
| Fragrance prepared according to Example VIII. | An herbal aroma with floral, rosey, green, woody, spicy, balsamic and cinnamin-like undertones. |

EXAMPLE X

Perfumed liquid detergents

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table II of Example IX, are prepared containing 0.10%, 0.15%, 0.20%, 0.25%, 0.30% and 0.35% of the substance set forth in Table II of Example IX. They are prepared by adding and homogeneously mixing the appropriate quantity of substance set forth in Table II of Example IX in the liquid detergent. The detergents all possess excellent aromas as set forth in Table II of Example IX, the intensity increasing with greater concentrations of substance as set forth in Table II of Example IX.

EXAMPLE XI

Preparation of colognes and handkerchief perfumes

Compositions as set forth in Table II of Example XI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XI are imparted to the colognes and to the handkerchief perfumes at all levels indicated.

EXAMPLE XII

Preparation of soap compositions

One hundred grams of soap chips [per sample] (IVORY ®, produced by the Procter & Gamble Company of Cincinnati, Ohio), are each mixed with one gram samples of substances as set forth in Table II of Example IX until homogenous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example IX.

EXAMPLE XIII

Preparation of solid detergent compositions

Detergents are prepared using the following ingredients according to Example I of Canadian Pat. No. 1,007,948 (incorporated by reference herein):

| Ingredient | Percent by Weight |
|---|---|
| "Neodol ® 45-11" (a $C_{14}$-$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IX. Each of the detergent samples has an excellent aroma as indicated in Table II of Example IX.

EXAMPLE XIV

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):

57% $C_{20-22}$ HAPS
22% isopropyl alcohol
20% antistatic agent
1% of one of the substances as set forth in Table II of Example IX, supra.

Fabric softening compositions prepared according to Example I at column 15 of U.S. Pat. No. 3,632,396 having aroma characteristics as set forth in Table II of Example IX, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example IX, supra, is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabric and these aroma characteristics are described in Table II of Example IX, supra.

EXAMPLE XV

Hair spray formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzeyl alcohol | 0.10 weight percent |
| Dow Corning 473 fluid prepared by the Dow Corning Corporation | 0.10 weight percent |
| Tween 20 surfactant prepared by ICI America Corporation | 0.03 weight percent |
| One of the perfumery substances as set forth in Table II of Example IX, supra | 0.10 weight percent |

The perfuming substances as set forth in Table II of Example IX, supra, add aroma characteristics as set forth in Table II of Example IX, supra, which are rather intense and esthetically pleasing to the users of the soft-feel, goodhold pump hair sprays.

EXAMPLE XVI

Conditioning shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 disterate produced by Armak Corporation. This material is "COMPOSITION B".

The resulting COMPOSITION A and COMPOSITION B are then mixed in a 50:50 wt ratio of A;B and cooled to 45° C. and 0.3 wt percent of perfuming substance as set forth in Table II of Example IX added to the mixture. The resulting mixture is cooled to 40° C. and blending is carried out for an additional one hour in each case. At the end of this blending period, the resulting material has a pleasant fragrance as indicated in Table II of Example IX.

What is claimed is:

1. The methyl carbonate having the structure:

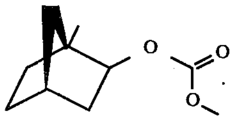

2. The methyl carbonate having the structure:

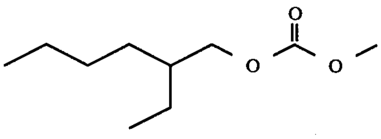

* * * * *